(12) United States Patent
McAlister

(10) Patent No.: US 8,187,550 B2
(45) Date of Patent: May 29, 2012

(54) REACTORS FOR CONDUCTING THERMOCHEMICAL PROCESSES WITH SOLAR HEAT INPUT, AND ASSOCIATED SYSTEMS AND METHODS

(75) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 13/027,181

(22) Filed: Feb. 14, 2011

(65) Prior Publication Data

US 2011/0198211 A1 Aug. 18, 2011

Related U.S. Application Data

(60) Provisional application No. 61/304,403, filed on Feb. 13, 2010.

(51) Int. Cl.
*B01J 19/08* (2006.01)
*F24J 2/46* (2006.01)

(52) U.S. Cl. ............ 422/186; 422/186.3; 126/569; 126/572; 126/600

(58) Field of Classification Search .......... 422/186, 422/186.3; 126/569, 572, 600
See application file for complete search history.

(56) References Cited

U.S. PATENT DOCUMENTS

| | | | |
|---|---|---|---|
| 4,019,868 A | 4/1977 | Sebacher et al. | |
| 4,053,576 A | 10/1977 | Fletcher | |
| 4,070,861 A | 1/1978 | Scragg et al. | |
| 4,099,489 A | 7/1978 | Bradley | |
| 4,138,993 A * | 2/1979 | Conley | 126/563 |
| 4,172,506 A | 10/1979 | Terry | |
| 4,229,184 A * | 10/1980 | Gregg | 48/62 R |
| 4,382,189 A | 5/1983 | Wilson | |
| 4,386,801 A | 6/1983 | Chapman et al. | |
| 4,455,045 A | 6/1984 | Wheeler | |

(Continued)

FOREIGN PATENT DOCUMENTS

EP 1658892 5/2006

OTHER PUBLICATIONS

First Action Interview Pilot Program Office Action for U.S. Appl. No. 13/027,015; Applicant: McAlister Technologies, LLC; Date of Mailing: Jul. 29, 2011, 4 pages.

(Continued)

*Primary Examiner* — Nina Bhat
(74) *Attorney, Agent, or Firm* — Perkins Coie LLP

(57) ABSTRACT

Reactors for conducting thermochemical processes with solar heat input, and associated systems and methods. A system in accordance with a particular embodiment include a reactor having a reaction zone, a reactant source coupled in fluid in communication with the reactant zone, and a solar concentrator having at least one concentrator surface positionable to direct solar energy to a focal area. The system can further include an actuator coupled to the solar concentrator to move the solar concentrator relative to the sun, and a controller operatively coupled to the actuator. The controller can be programmed with instructions that, when executed, direct the actuator to position the solar concentrator to focus the solar energy on the reaction zone when the solar energy is above a threshold level, and direct the actuator to position the solar concentrator to point to a location in the sky having relatively little radiant energy to cool an object positioned at the focal area when the solar energy is below the threshold level.

18 Claims, 6 Drawing Sheets

U.S. PATENT DOCUMENTS

| | | | |
|---|---|---|---|
| 4,549,528 A * | 10/1985 | Gibson | 588/306 |
| 4,601,508 A | 7/1986 | Kerian | |
| 4,611,847 A | 9/1986 | Sullivan | |
| 4,706,651 A | 11/1987 | Yudow | |
| 4,746,160 A | 5/1988 | Wiesemeyer | |
| 4,921,580 A * | 5/1990 | Martes et al. | 202/205 |
| 4,978,162 A | 12/1990 | Labbe | |
| 5,058,945 A | 10/1991 | Elliott, Sr. et al. | |
| 5,119,897 A | 6/1992 | Moriwake | |
| 5,222,698 A | 6/1993 | Nelson et al. | |
| 5,280,990 A | 1/1994 | Rinard | |
| 5,348,774 A | 9/1994 | Golecki et al. | |
| 5,407,245 A | 4/1995 | Geropp | |
| 5,498,059 A | 3/1996 | Switlik | |
| 5,560,443 A | 10/1996 | DuBose | |
| 5,647,877 A * | 7/1997 | Epstein | 48/210 |
| 5,882,382 A | 3/1999 | Hachisuka et al. | |
| 5,986,429 A | 11/1999 | Mula, Jr. | |
| 6,068,328 A | 5/2000 | Gazdzinski | |
| 6,081,183 A | 6/2000 | Mading et al. | |
| 6,089,224 A * | 7/2000 | Poulek | 126/576 |
| 6,092,861 A | 7/2000 | Whelan | |
| 6,155,212 A | 12/2000 | McAlister | |
| 6,200,069 B1 | 3/2001 | Miller | |
| 6,216,599 B1 | 4/2001 | Cavanagh | |
| 6,220,193 B1 | 4/2001 | Dilks | |
| 6,242,752 B1 | 6/2001 | Soma et al. | |
| 6,309,010 B1 | 10/2001 | Whitten | |
| 6,378,932 B1 | 4/2002 | Fasel et al. | |
| 6,409,252 B1 | 6/2002 | Andrus | |
| 6,464,755 B2 | 10/2002 | Nakanishi et al. | |
| 6,502,533 B1 | 1/2003 | Meacham | |
| 6,508,209 B1 | 1/2003 | Collier, Jr. | |
| 6,585,785 B1 | 7/2003 | Warren et al. | |
| 6,749,043 B2 | 6/2004 | Brown et al. | |
| 6,756,140 B1 | 6/2004 | McAlister | |
| 6,838,782 B2 | 1/2005 | Vu | |
| 6,854,788 B1 | 2/2005 | Graham | |
| 6,897,575 B1 | 5/2005 | Yu | |
| 6,926,345 B2 | 8/2005 | Ortega et al. | |
| 6,979,049 B2 | 12/2005 | Ortega et al. | |
| 7,033,570 B2 * | 4/2006 | Weimer et al. | 423/650 |
| 7,140,181 B1 * | 11/2006 | Jensen et al. | 60/641.8 |
| 7,152,908 B2 | 12/2006 | Shahbazi | |
| 7,165,804 B2 | 1/2007 | Shahbazi | |
| 7,185,944 B2 | 3/2007 | Shahbazi | |
| 7,207,620 B2 | 4/2007 | Cosgrove et al. | |
| 7,210,467 B2 | 5/2007 | Kweon et al. | |
| 7,211,905 B1 | 5/2007 | McDavid, Jr. | |
| 7,237,827 B2 | 7/2007 | Shahbazi | |
| 7,243,980 B2 | 7/2007 | Vala | |
| 7,293,533 B2 | 11/2007 | Hemsath | |
| 7,449,158 B2 | 11/2008 | Haueter et al. | |
| 7,568,479 B2 * | 8/2009 | Rabinowitz | 126/600 |
| 7,628,137 B1 | 12/2009 | McAlister | |
| 7,884,308 B1 * | 2/2011 | Mejia | 250/203.4 |
| 7,955,478 B2 * | 6/2011 | McClure | 203/10 |
| 2001/0000889 A1 | 5/2001 | Yadav et al. | |
| 2003/0019104 A1 | 1/2003 | Smalc | |
| 2003/0042128 A1 | 3/2003 | Harutyunyan et al. | |
| 2003/0182861 A1 | 10/2003 | Weimer et al. | |
| 2004/0033455 A1 | 2/2004 | Tonkovich et al. | |
| 2004/0265448 A1 | 12/2004 | Shiau et al. | |
| 2004/0266615 A1 | 12/2004 | Watson et al. | |
| 2005/0272856 A1 | 12/2005 | Cooper et al. | |
| 2006/0005738 A1 | 1/2006 | Kumar | |
| 2006/0005739 A1 | 1/2006 | Kumar | |
| 2006/0048808 A1 | 3/2006 | Ruckman et al. | |
| 2007/0138006 A1 | 6/2007 | Oakes et al. | |
| 2007/0214986 A1 | 9/2007 | Gaus et al. | |
| 2008/0086946 A1 | 4/2008 | Weimer et al. | |
| 2008/0175766 A1 * | 7/2008 | Mankins et al. | 422/186 |
| 2008/0295883 A1 | 12/2008 | Ducellier et al. | |
| 2008/0314411 A1 * | 12/2008 | Mueller et al. | 134/22.1 |
| 2009/0232716 A1 | 9/2009 | Rohrich et al. | |
| 2009/0313886 A1 * | 12/2009 | Hinman et al. | 44/302 |
| 2010/0107994 A1 | 5/2010 | Moriarty et al. | |

OTHER PUBLICATIONS

"Carnot Thermochemical Cycles." Digital image. Wikipedia, the Free Encyclopedia, Published: Aug. 31, 2010. Accessed: Jan. 4, 2011. Printed: May 20, 2011. <http://en.wikipedia.org/wiki/File:Carnot_thermochemical_cycles.PNG>. p. 1.

"Closed Loop Thermochemical Energy Storage System Using Ammonia." Australian National University College of Engineering & Computer Science—Solar Thermal Group. Accessed: Jan. 4, 2011. Printed: May 20, 2011. <http://solar-thermal.anu.edu.au/high-temperature/thermochemical-energy-storage/>. pp. 1-2.

"SI Cycle." Digital image. Sandia National Laboratories: Energy, Resources and Nonproliferation. Accessed: Jan. 4, 2011. Printed: Jun. 13, 2011. <http://www.sandia.gov/ERN/images/SI-cycle2.jpg>. p. 1.

"Solar Hydrogen." Digital image. Swiss Federal Institute of Technology, Department of Mechanical and Process Engineering, Zurich. Accessed: Jan. 4, 2011. Printed: May 23, 2011. p. 1, <http://www.pre.ethz.ch/research/projects/imgs/solarhydro_1.jpg>.

"The Solar Zinc Route." Digital image. Swiss Federal Institute of Technology, Department of Mechanical and Process Engineering, Zurich. Accessed: Jan. 4, 2011. Printed: May 20, 2011. <http://www.pre.ethz.ch/research/projects/imgs/solzinc_1.jpg>. p. 1.

"Zinc Zinc-oxide Thermochemical Cycle." Digital image. Wikipedia, the Free Encyclopedia, Published: Dec. 21, 2008. Accessed: Jan. 4, 2011. Printed: May 20, 2011. <http://en.wikipedia.org/wiki/File:Zinc_zinc-oxide_thermochemical_cycle.jpg>. p. 1.

Chen et al. "Parylene-Encapsulated Copolymeric Membranes as Localized and Sustained Drug Delivery Platforms." Annals of Biomedical Engineering, vol. 37, Issue 10 (Oct. 2009): pp. 2003-2017.

Chen et al. Thermochemistry Concept Map. Teacherknowledge Wikispace, Published: Nov. 20, 2006. <http://teacherknowledge.wikispaces.com/file/view/Thermochemistry+concept+map+-+Extended.pdf>. p. 1.

Food and Agriculture Organization of the United Nations. "Carbon Sequestration Options under the Clean Development Mechanism to Address Land Degradation." World Soil Resources Reports. Rome, 2000. pp. 1-45.

Foust et al. "An Economic and Environmental Comparison of a Biochemical and a Thermochemical Lignocellulosic Ethanol Conversion Processes." Cellulose, vol. 16, Issue 4. Jun. 10, 2009. pp. 547-565.

Funk, James E. "Thermochemical Processes for the Production of Hydrogen from Water." College of Engineering, University of Kentucky, Lexington, Kentucky. 1975. pp. 1-9.

Hackett et al. "Evaluation of Conversion Technoloigy Processes and Products: Appendix A—Discussion of Thermochemical Process Definitions." University of California, Davis: Sep. 2004. pp. 1-7.

US Environmental Protection Agency. "Carbon Dioxide | Climate Change—Greenhouse Gas Emissions | U.S. EPA". Web. Accessed: Jul. 1, 2010. Printed: Jun. 13, 2011. 1 Page. <http://www.epa.gov/climatechange/emissions/co2.html>.

U.S. Energy Information Administration."Greenhouse Gases—Energy Explained, Your Guide to Understanding Energy." Web. Accessed: Jul. 1, 2010. Printed: Jun. 13, 2011. 1 Pages. <http://www.eia.gov/energyexplained/index.cfm?page=environment_about_ghg>.

"The Carbon Cycle : Feature Articles." NASA Earth Observatory : Home. Web. Accessed: Jul. 1, 2010. Printed: Jun. 13, 2011. 12 Pages. <http://earthobservatory.nasa.gov/Features/CarbonCycle>.

Kasting, James F. "The Carbon Cycle, Climate, and the Long-Term Effects of Fossil Fuel Burning." U.S. Global Change Research Information Office. 1998. Web. Accessed: Jul. 1, 2010. Printed: Jun. 13, 2011. <http://www.gcrio.org/CONSEQUENCES/vol4no1/carbcycle.html>.

US Environmental Protection Agency. "Cap and Trade." Web. Accessed: Jul. 1, 2010. Printed: Jun. 13, 2011. <http://www.epa.gov/captrade/>.

US Environmental Protection Agency. "EPA Preliminary Analysis of the Waxman-Markey Discussion Draft". Web. Published: Apr. 20, 2009. Accessed: Jul. 1, 2010. Printed: Jun. 13, 2011. <http://www.epa.gov/climatechange/economics/pdfs/WM-Analysis.pdf>.

US Environmental Protection Agency. "Carbon Dioxide—Geologic Sequestration | Climate Change—Greenhouse Gas Emissions | U.S. EPA." Web. Accessed: Jul. 1, 2010. Printed: Jun. 13, 2011. <http://www.epa.gov/climatechange/emissions/co2_geosequest.html>.

First Action Interview Pilot Program Office Action for U.S. Appl. No. 13/026,990; Applicant: McAlister Technologies, LLC; Date of Mailing: Nov. 16, 2011; 15 pages.

First Action Interview Pilot Program Office Action for U.S. Appl. No. 13/026,996; Applicant: McAlister Technologies, LLC; Date of Mailing: Oct. 27, 2011; 19 pages.

First Action Interview Pilot Program Office Action for U.S. Appl. No. 13/027,015; Applicant: McAlister Technologies, LLC; Date of Mailing: Oct. 6, 2011, 4 pages.

First Action Interview Pilot Program Office Action for U.S. Appl. No. 13/027,215; Applicant: McAlister Technologies, LLC; Date of Mailing: Oct. 27, 2011; 3 pages.

International Search Report and Written Opinion for PCT Application No. PCT/US11/024796; Applicant: McAlister Technologies, LLC; Date of Mailing: Oct. 25, 2011; 13 pages.

* cited by examiner

REACTORS FOR CONDUCTING THERMOCHEMICAL PROCESSES WITH SOLAR HEAT INPUT, AND ASSOCIATED SYSTEMS AND METHODS

CROSS-REFERENCE TO RELATED APPLICATIONS

The present application claims priority to U.S. Provisional Application 61/304,403, filed Feb. 13, 2010 and incorporated herein by reference. To the extent the foregoing application and/or any other materials incorporated herein by reference conflict with the disclosure presented herein, the disclosure herein controls.

TECHNICAL FIELD

The present technology is directed generally to reactors for conducting thermochemical processes with solar heat input, and associated systems and methods. In particular embodiments, such reactors can be used to produce clean-burning, hydrogen-based fuels from a wide variety of feedstocks, and can produce structural building blocks from carbon and/or other elements that are released when forming the hydrogen-based fuels.

BACKGROUND

Renewable energy sources such as solar, wind, wave, falling water, and biomass-based sources have tremendous potential as significant energy sources, but currently suffer from a variety of problems that prohibit widespread adoption. For example, using renewable energy sources in the production of electricity is dependent on the availability of the sources, which can be intermittent. Solar energy is limited by the sun's availability (i.e., daytime only), wind energy is limited by the variability of wind, falling water energy is limited by droughts, and biomass energy is limited by seasonal variances, among other things. As a result of these and other factors, much of the energy from renewable sources, captured or not captured, tends to be wasted.

The foregoing inefficiencies associated with capturing and saving energy limit the growth of renewable energy sources into viable energy providers for many regions of the world, because they often lead to high costs of producing energy. Thus, the world continues to rely on oil and other fossil fuels as major energy sources because, at least in part, government subsidies and other programs supporting technology developments associated with fossil fuels make it deceptively convenient and seemingly inexpensive to use such fuels. At the same time, the replacement cost for the expended resources, and the costs of environment degradation, health impacts, and other by-products of fossil fuel use are not included in the purchase price of the energy resulting from these fuels.

In light of the foregoing and other drawbacks currently associated with sustainably producing renewable resources, there remains a need for improving the efficiencies and commercial viabilities of producing products and fuels with such resources

DETAILED DESCRIPTION

1. Overview

Figure 1:
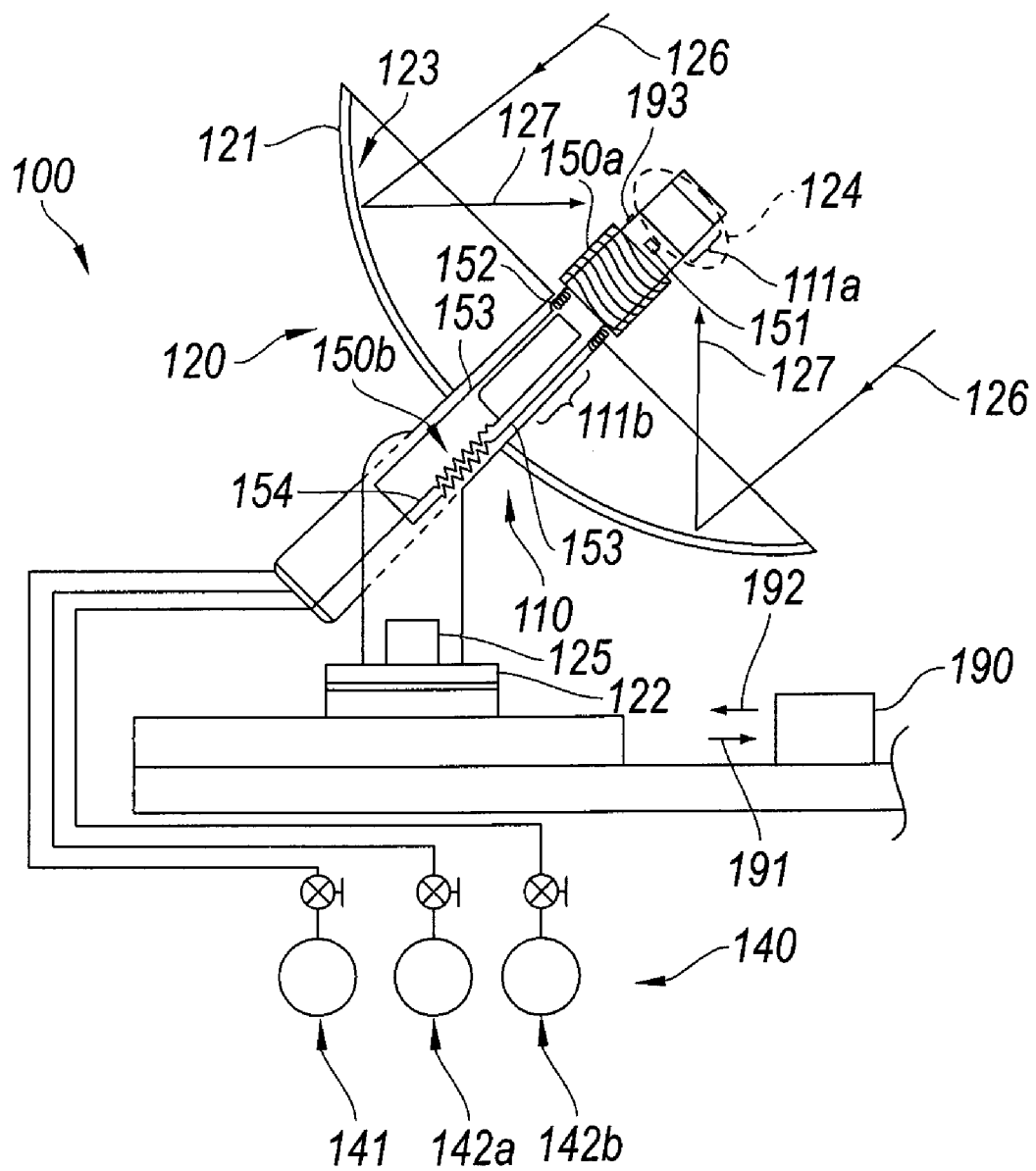
FIG. 1 is a partially schematic, partial cross-sectional illustration of a system having a solar concentrator configured in accordance with an embodiment of the present technology.

Several examples of devices, systems and methods for conducting reactions driven by solar energy are described below. Reactors in accordance with particular embodiments can collect solar energy during one phase of operation and use the collection device to reject heat during another phase of operation. Such reactors can be used to produce hydrogen fuels and/or other useful end products. Accordingly, the reactors can produce clean-burning fuel and can re-purpose carbon and/or other constituents for use in durable goods, including polymers and carbon composites. Although the following description provides many specific details of the following examples in a manner sufficient to enable a person skilled in the relevant art to practice, make and use them, several of the details and advantages described below may not be necessary to practice certain examples of the technology. Additionally, the technology may include other examples that are within the scope of the claims but are not described here in detail.

References throughout this specification to "one example," "an example," "one embodiment" or "an embodiment" mean that a particular feature, structure, process or characteristic described in connection with the example is included in at least one example of the present technology. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any suitable manner in one or more examples of the technology. The headings provided herein are for convenience only and are not intended to limit or interpret the scope or meaning of the claimed technology.

Certain embodiments of the technology described below may take the form of computer-executable instructions, including routines executed by a programmable computer or controller. Those skilled in the relevant art will appreciate that the technology can be practiced on computer or controller systems other than those shown and described below. The technology can be embodied in a special-purpose computer, controller, or data processor that is specifically programmed, configured or constructed to perform one or more of the computer-executable instructions described below. Accordingly, the terms "computer" and "controller" as generally used herein refer to any data processor and can include internet appliances, hand-held devices, multi-processor systems, programmable consumer electronics, network computers, mini-computers, and the like. The technology can also be practiced in distributed environments where tasks or modules are performed by remote processing devices that are linked through a communications network. Aspects of the technology described below may be stored or distributed on computer-readable media, including magnetic or optically readable or removable computer discs as well as media distributed electronically over networks. In particular embodiments, data structures and transmissions of data particular to aspects of the technology are also encompassed within the scope of the present technology. The present technology encompasses both methods of programming computer-readable media to perform particular steps, as well as executing the steps.

A reactor system in accordance with a particular embodiment includes a reactor having a reaction zone, a reactant source coupled in fluid communication with the reaction zone, and a solar collector having a least one concentrator surface positionable to direct solar energy to a focal area. The system can further include an actuator coupled to the solar concentrator to move the solar concentrator relative to the sun, and a controller operatively coupled to the actuator to control its operation. The controller can be programmed with instructions that, when executed, direct the actuator to position the solar concentrator to focus the solar energy on the reaction zone when the solar energy is above a threshold level (e.g. during the day). When the solar energy is below the threshold level, the controller can direct the actuator to position the solar concentrator to point to a location in the sky having relatively little radiant energy to cool an object positioned at the focal area.

A system in accordance with another embodiment of the technology includes a reactor, a reactant source, a solar concentrator, and a first actuator coupled to the solar concentrator to move the solar concentrator relative to the sun. The system can further include a radiation control structure positioned between a concentrator surface of the solar concentrator and its associated focal area. The radiation control structure has first surface and a second surface facing away from the first surface, each with a different absorptivity and emissivity. In particular, the first surface can have a first radiant energy absorptivity and a first radiant energy emissivity, and the second surface can have a second radiant energy absorptivity less than the first radiant energy absorptivity, and a second radiant energy emissivity greater than the first radiant energy emissivity. The system can further include a second actuator coupled to the radiation control structure to change the structure from a first configuration in which the first surface faces toward the concentrator surface, and a second configuration in which the second surface faces toward the concentrator surface. In particular embodiments, the system can still further include a controller that directs the operation of the radiation control structure depending upon the level of solar energy directed by the solar concentrator.

A method in accordance with a particular embodiment of the technology includes concentrating solar energy with a solar concentrator, directing the concentrated solar energy to a reaction zone positioned at a focal area of the solar concentrator, and at the reaction zone, dissociating a hydrogen donor into dissociation products via the concentrated solar energy. From the dissociation products, the method can further include providing at least one of a structural building block (based on at least one of carbon, nitrogen, boron, silicon sulfur, and a transition metal) and hydrogen-based fuel. In further particular embodiments, the method can further include taking different actions depending upon whether the solar energy is above or below a threshold level. For example, when the solar energy is above a threshold level, it can be directed to the reaction zone, and when it is below the threshold level, the solar concentrator can be pointed away from the sun to a location in the sky having relatively little radiative energy to cool the structural building block and/or the hydrogen based fuel.

2. Representative Reactors and Associated Methodologies

FIG. 1 is a partially schematic, partial cross-sectional illustration of a system 100 having a reactor 110 coupled to a solar concentrator 120 in accordance with the particular embodiment of the technology. In one aspect of this embodiment, the solar concentrator 120 includes a dish 121 mounted to pedestal 122. The dish 121 can include a concentrator surface 123 that receives incident solar energy 126, and directs the solar energy as focused solar energy 127 toward a focal area 124. The dish 121 can be coupled to a concentrator actuator 125 that moves the dish 121 about at least two orthogonal axes in order to efficiently focus the solar energy 126 as the earth rotates. As will be described in further detail below, the concentrator actuator 125 can also be configured to deliberately position the dish 121 to face away from the sun during a cooling operation.

The reactor 110 can include one or more reaction zones 111, shown in FIG. 1 as a first reaction zone 111a and second reaction zone 111b. In a particular embodiment, the first reaction zone 111a is positioned at the focal area 124 to receive the focused solar energy 127 and facilitate a dissociation reaction or other endothermic reaction. Accordingly, the system 100 can further include a distribution/collection system 140 that provides reactants to the reactor 110 and collects products received from the reactor 110. In one aspect of this embodiment, the distribution/collection system 140 includes a reactant source 141 that directs a reactant to the first reaction zone 111a, and one or more product collectors 142 (two are shown in FIG. 1 as a first product collector 142a and a second product collector 142b) that collect products from the reactor 110. When the reactor 110 includes a single reaction zone (e.g. the first reaction zone 111a) the product collectors 142a, 142b can collect products directly from the first reaction zone 111a. In another embodiment, intermediate products produced at the first reaction zone 111a are directed to the second reaction zone 111b. At the second reaction zone 111b, the intermediate products can undergo an exothermic reaction, and the resulting products are then delivered to the product collectors 142a, 142b along a product flow path 154. For example, in a representative embodiment, the reactant source 141 can include methane and carbon dioxide, which are provided (e.g., in an individually controlled manner) to the first reaction zone 111a and heated to produce carbon monoxide and hydrogen. The carbon monoxide and hydrogen are then provided to the second reaction zone 111b to produce methanol in an exothermic reaction. Further details of this arrangement and associated heat transfer processes between the first reaction zone 111a and second reaction zone 111b are described in more detail in co-pending U.S. application Ser. No. 13/027,060 titled "REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS" filed concurrently herewith and incorporated herein by reference.

In at least some instances, it is desirable to provide cooling to the reactor 110, in addition to the solar heating described above. For example, cooling can be used to remove heat produced by the exothermic reaction being conducted at the second reaction zone 111b and thus allow the reaction to continue. When the product produced at the second reaction zone 111b includes methanol, it may desirable to further cool the methanol to a liquid to provide for convenient storage and transportation. Accordingly, the system 100 can include features that facilitate using the concentrator surface 123 to cool components or constituents at the reactor 110. In a particular embodiment, the system 100 includes a first heat exchanger 150a operatively coupled to a heat exchanger actuator 151b that moves the first heat exchanger 150a relative to the focal area 124. The first heat exchanger 150a can include a heat exchanger fluid that communicates thermally with the constituents in the reactor 110, but is in fluid isolation from these constituents to avoid contaminating the constituents and/or interfering with the reactions taking place in the reactor 110. The heat exchanger fluid travels around a heat exchanger fluid flow path 153 in a circuit from the first heat exchanger 150a to a second heat exchanger 150b and back. At the second heat exchanger 150b, the heat exchanger fluid receives heat from the product (e.g. methanol) produced by the reactor 110 as the product proceeds from the second reaction zone 111b to the distribution/collection system 140. The heat exchanger fluid flow path 153 delivers the heated heat exchanger fluid back to the first heat exchanger 150a for cooling. One or more strain relief features 152 in the heat exchanger fluid flow path 153 (e.g., coiled conduits) facilitate the movement of the first heat exchanger 150a. The system 100 can also include a controller 190 that receives input signals 191 from any of a variety of sensors, transducers, and/or other elements of the system 100, and, in response to information received from these elements, delivers control signals 192 to adjust operational parameters of the system 100.

Figure 2:
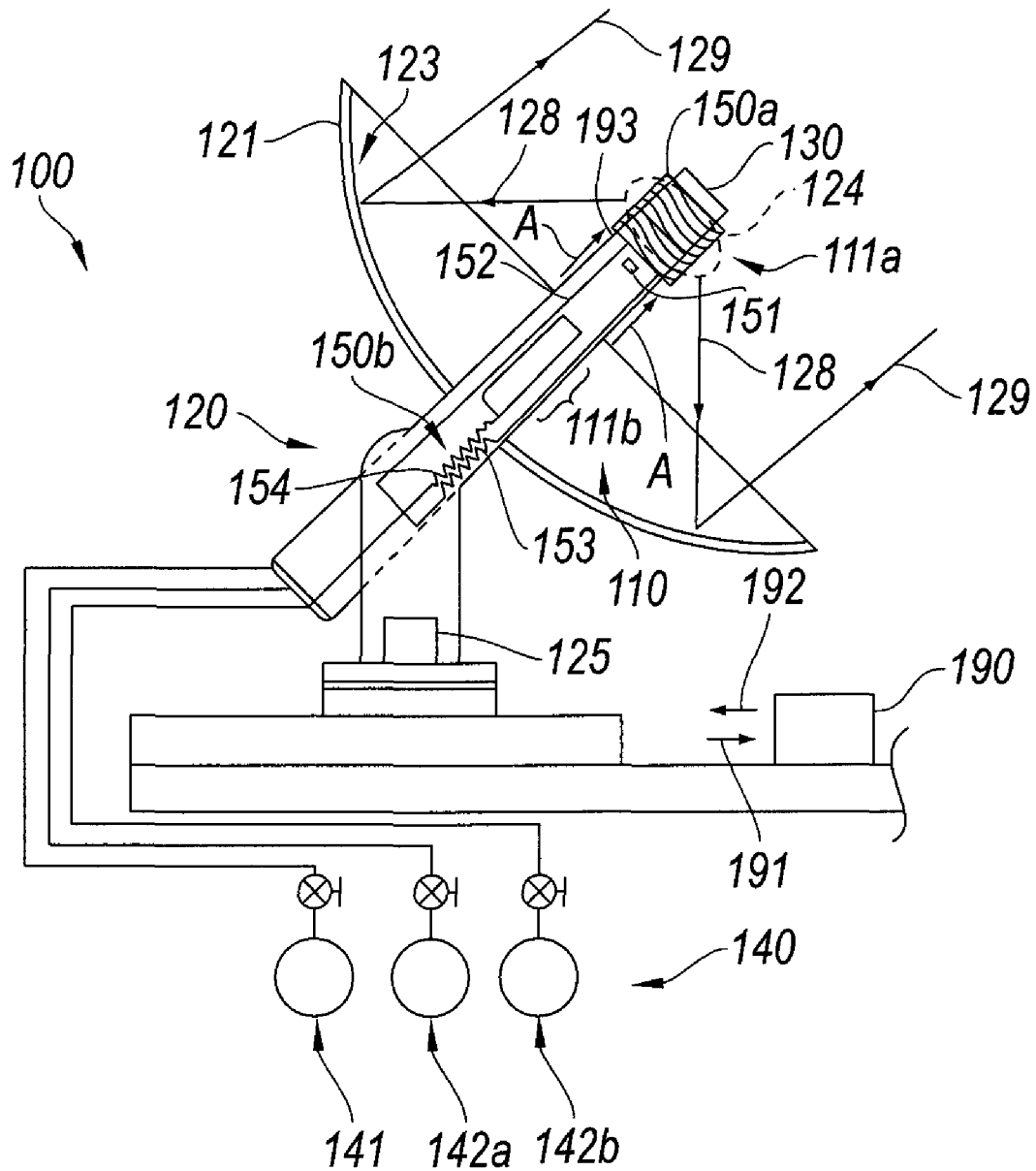
FIG. 2 is a partially schematic, partial cross-sectional illustration of an embodiment of the system shown in FIG. 1 with the solar concentrator configured to emit energy in a cooling process, in accordance with an embodiment of the disclosure.

FIG. 2 illustrates one mechanism by which the heat exchanger fluid provided to the first heat exchanger 150a is cooled. In this embodiment, the controller 190 directs the heat exchanger actuator 151 to drive the first heat exchanger 150a from the position shown in FIG. 1 to the focal area 124, as indicated by arrows A. In addition, the controller 190 can direct the concentrator actuator 125 to position the dish 121 so that the concentrator surface 123 points away from the sun and to an area of the sky having very little radiant energy. In general, this process can be completed at night, when it is easier to avoid the radiant energy of the sun and the local environment, but in at least some embodiments, this process can be conducted during the daytime as well. A radiant energy sensor 193 coupled to the controller 190 can detect when the incoming solar radiation passes below a threshold level, indicating a suitable time for positioning the first heat exchanger 150a in the location shown in FIG. 2.

With the first heat exchanger 150a in the position shown in FIG. 2, the hot heat transfer fluid in the heat exchanger 150a radiates emitted energy 128 that is collected by the dish 121 at the concentrator surface 123 and redirected outwardly as directed emitted energy 129. An insulator 130 positioned adjacent to the focal area 124 can prevent the radiant energy from being emitted in direction other than toward the concentrator surface 123. By positioning the concentrator surface 123 to point to a region in space having very little radiative energy, the region in space can operate as a heat sink, and can accordingly receive the directed emitted energy 129 rejected by the first heat exchanger 150a. The heat exchanger fluid, after being cooled at the first heat exchanger 150a returns to the second heat exchanger 150b to absorb more heat from the product flowing along the product flow path 154. Accordingly, the concentrator surface 123 can be used to cool as well as to heat elements of the reactor 110.

In a particular embodiment, the first heat exchanger 150a is positioned as shown in FIG. 1 during the day, and as positioned as shown in FIG. 2 during the night. In other embodiments, multiple systems 100 can be coupled together, some with the corresponding first heat exchanger 150a positioned as shown in FIG. 1, and others with the first heat exchanger 150a positioned as shown in FIG. 2, to provide simultaneous heating and cooling. In any of these embodiments, the cooling process can be used to liquefy methanol, and/or provide other functions. Such functions can include liquefying or solidifying other substances, e.g., carbon dioxide, ethanol, butanol or hydrogen.

In particular embodiments, the reactants delivered to the reactor 110 are selected to include hydrogen, which is dissociated from the other elements of the reactant (e.g. carbon, nitrogen, boron, silicon, a transition metal, and/or sulfur) to produce a hydrogen-based fuel (e.g. diatomic hydrogen) and a structural building block that can be further processed to produce durable goods. Such durable goods include graphite, graphene, and/or polymers, which may produced from carbon structural building blocks, and other suitable compounds formed from hydrogenous or other structural building blocks. Further details of suitable processes and products are disclosed in the following co-pending U.S. patent application Ser. No. 13/027,208 titled "CHEMICAL PROCESSES AND REACTORS FOR EFFICIENTLY PRODUCING HYDROGEN FUELS AND STRUCTURAL MATERIALS, AND ASSOCIATED SYSTEMS AND METHODS"; Ser. No. 13/027,214 titled "ARCHITECTURAL CONSTRUCT HAVING FOR EXAMPLE A PLURALITY OF ARCHITECTURAL CRYSTALS"; and Ser. No. 13/027,068 titled "CARBON-BASED DURABLE GOODS AND RENEWABLE FUEL FROM BIOMASS WASTE DISSOCIATION", all of which are filed concurrently herewith and incorporated herein by reference.

Figure 3:
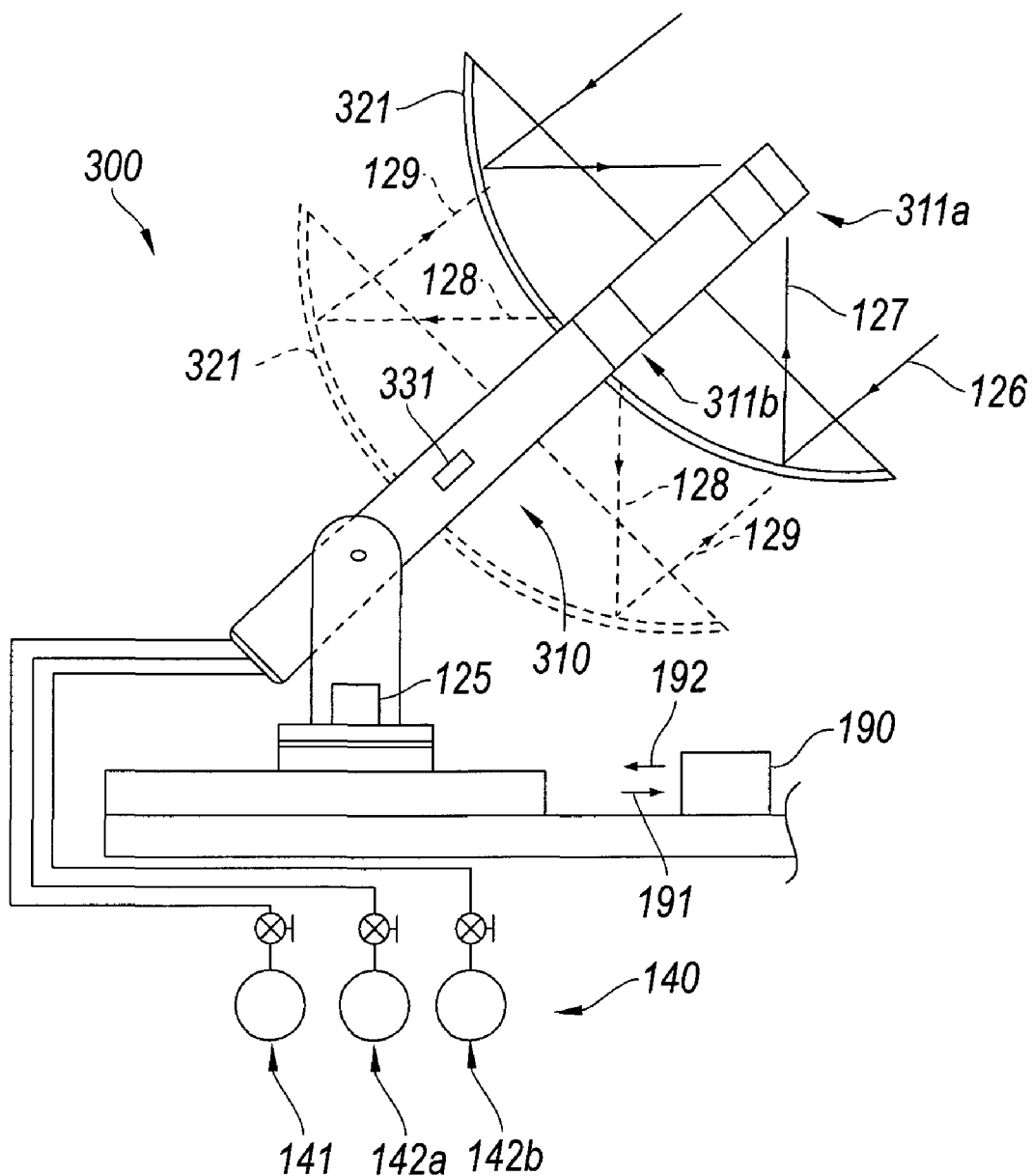
FIG. 3 is a partially schematic, partial cross-sectional illustration of a system having a movable solar concentrator dish in accordance with an embodiment of the disclosure.

FIG. 3 illustrates a system 300 having a reactor 310 with a movable dish 321 configured in accordance another embodiment of the disclosed technology. In a particular aspect of this embodiment, the reactor 310 includes a first reaction zone 311a and a second reaction zone 311b, with the first reaction zone 311a receiving focused solar energy 127 when the dish 321 has a first position, shown in solid lines in FIG. 3. The dish 321 is coupled to a dish actuator 331 that moves the dish 321 relative to the reaction zones 311a, 311b. Accordingly, during a second phase of operation, the controller 190 directs the dish actuator 331 to move the dish 321 to the second position shown in dashed lines in FIG. 3. In one embodiment, this arrangement can be used to provide heat to the second reaction zone 311b when the dish 321 is in the second position. In another embodiment, this arrangement can be used to cool the second reaction zone 311b. Accordingly, the controller 190 can direct the concentrator actuator 125 to point the dish 321 to a position in the sky having little or no radiant energy, thus allowing the second reaction zone 311b to reject heat to the dish 321 and ultimately to space, in a manner generally similar to that described above with reference to FIGS. 1 and 2.

Figure 4:
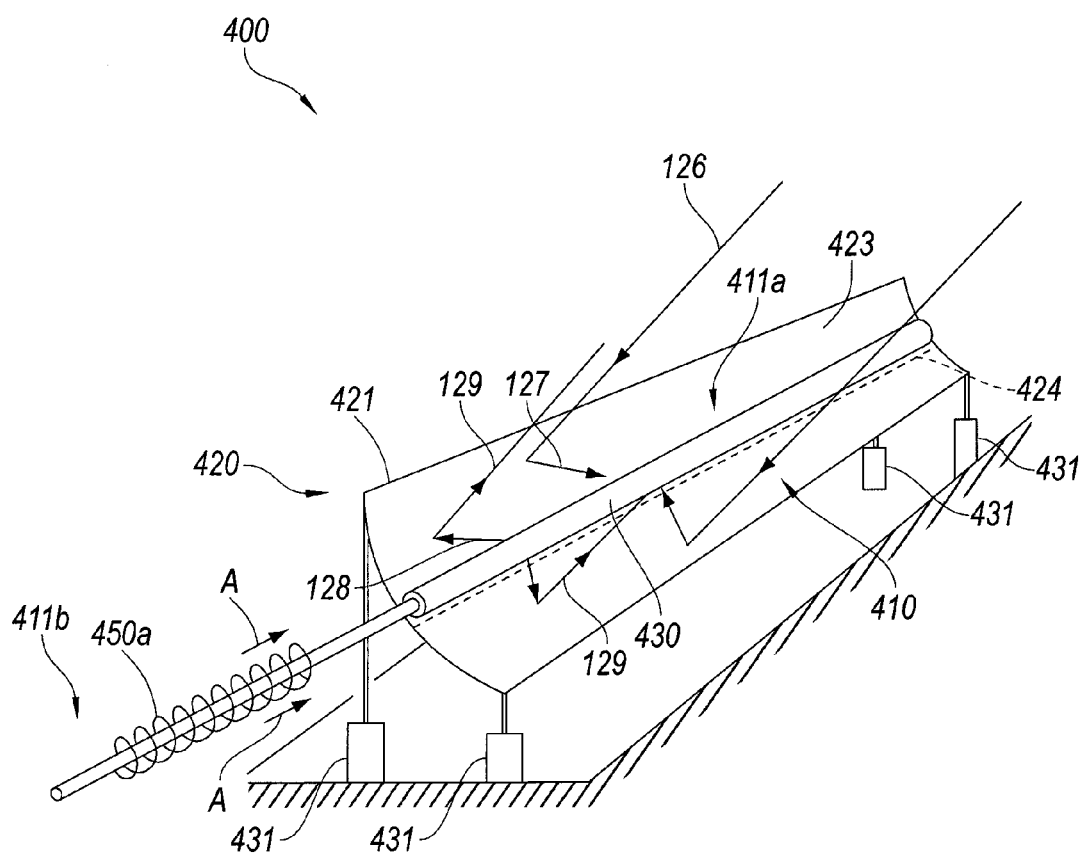
FIG. 4 is a partially schematic, isometric illustration of a system having a trough-shaped solar concentrator in accordance with an embodiment of the disclosure.

In other embodiments, the systems can include solar collectors having arrangements other than a dish arrangement. For example, FIG. 4 illustrates a system 400 having a reactor 410 that is coupled to a solar concentrator 420 in the form of a trough 421. The trough 421 is rotated by one or more trough actuators 431, and includes a concentrator surface 423 that directs incident solar energy 126 toward the reactor 410 for heating. In a particular embodiment shown in FIG. 4, the reactor 410 can include a first reaction zone 411a and a second reaction zone 411b that can operate in a manner generally similar to that described above with reference to FIGS. 1 and 2. The system 400 can further include a first heat exchanger 450a that can be moved toward or away from a focal area 424 provided by the trough 421 at the underside of the reactor 410. Accordingly, the first heat exchanger 450a can be positioned as shown FIG. 4 when the incident solar energy 126 is directed to the first reaction 411a for heating, and can be moved over the focal area 424 (as indicated by arrows A) to reject heat in a manner generally similar to that described above with respect to FIGS. 1 and 2. The reactor 410 can include an insulator 430 positioned to prevent heat losses from the reactor 410 during heating. The insulator 430 can also prevent heat from leaving the reactor 410 other than along the emitted energy path 128, in manner generally similar to that described above.

Figure 5:
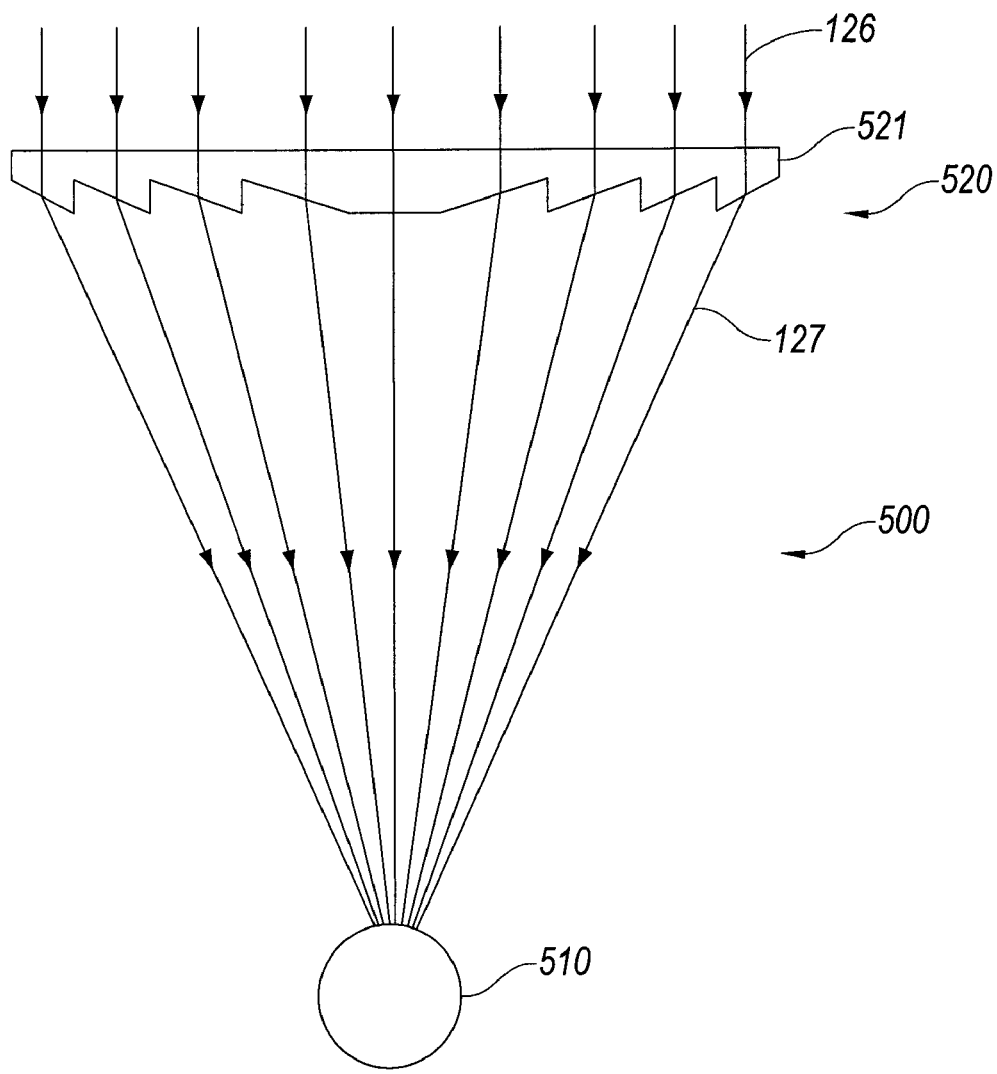
FIG. 5 is a partially schematic illustration of a system having a Fresnel lens concentrator in accordance with an embodiment of the disclosure.

FIG. 5 is a partially schematic illustration of a system 500 that includes a solar concentrator 520 having a Fresnel lens 521 positioned to receive incident solar energy 126 and deliver focused solar energy 127 to a reactor 510. This arrangement can be used in conjunction with any of the systems and components described above for heating and/or cooling constituents and/or components of the reactor 510.

Figure 6:
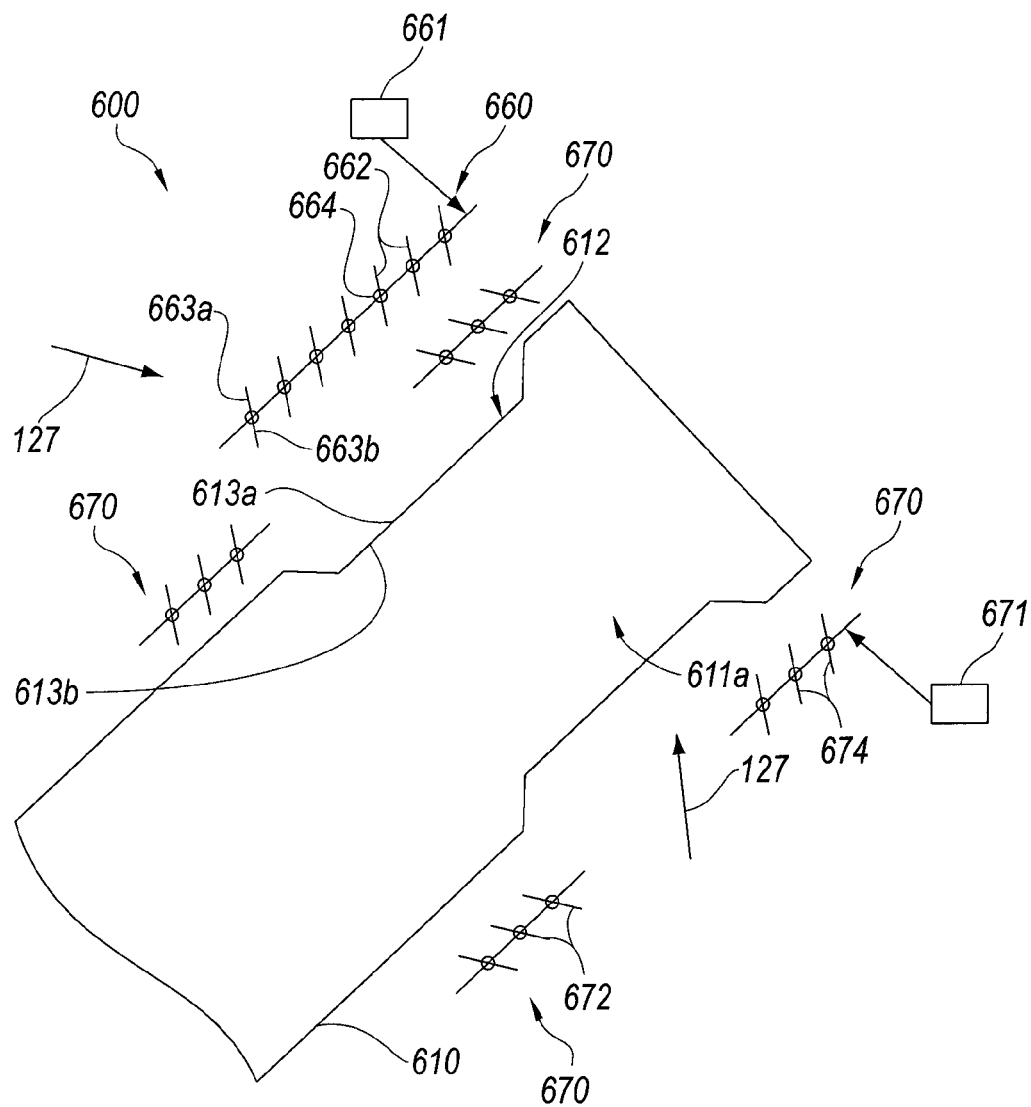
FIG. 6 is a partially schematic illustration of a reactor having a radiation control structure and redirection components configured in accordance with an embodiment of the present technology.

FIG. 6 is partially schematic illustration of a system 600 having a reactor 610 that receives radiation in accordance with still further embodiments of the disclosed technology. In one aspect of these embodiments, the reactor 610 can have an overall layout generally similar to that described above with reference to FIGS. 1 and 2. In other embodiments, the reactor can be configured like those shown in any of FIGS. 3-5, with the components described below operating in a generally similar manner.

The reactor 610 can include a transmissive component 612 that allows focused solar energy 127 to enter a first reaction zone 611a. In one embodiment, the transmissive component 112 includes glass or another material that is highly transparent to solar radiation. In another embodiment, the transmissive component 612 can include one or more elements that absorb energy (e.g., radiant energy) at one wavelength and re-radiate energy at another wavelength. For example, the transmissive component 612 can include a first surface 613a that receives incident solar energy at one wavelength and a second surface 613b that re-radiates the energy at another wavelength into the first reaction zone 611a. In this manner, the energy provided to the first reaction zone 611a can be specifically tailored to match or approximate the absorption characteristics of the reactants and/or products placed within the first reaction zone 611a. For example, the first and second surfaces 613a, 613b can be configured to receive radiation over a first spectrum having a first peak wavelength range and re-radiate the radiation into the first reaction zone 611a over a second spectrum having a second peak wavelength range different than the first. The second peak wavelength range can, in particular embodiments be closer than the first to the peak absorption of a reactant or product in the first reaction zone 611a. Further details of representative re-radiation devices are described in co-pending U.S. patent application Ser. No. 13/027,015 titled "CHEMICAL REACTORS WITH RE-RADIATING SURFACES AND ASSOCIATED SYSTEMS AND METHODS" filed concurrently herewith and incorporated herein by reference.

In particular embodiments, the system can also include a radiation control structure 660 powered by a control structure actuator 661. The radiation control structure 660 can include multiple movable elements 662, e.g. panels that pivot about corresponding pivot joints 664 in the manner of a Venetian blind. One set of elements 662 is shown in FIG. 6 for purposes of illustration—in general, this set is duplicated circumferentially around the radiation-receiving surfaces of the reactor 610. Each movable element 662 can have a first surface 663a and a second surface 663b. Accordingly, the radiation control structure 660 can position one surface or the other to face outwardly, depending upon external conditions (e.g. the level of focused solar energy 127), and/or whether the reactor 610 is being used in a heating mode or a cooling mode. In a particular aspect of this embodiment, the first surface 663a can have a relatively high absorptivity and a relatively low emissivity. This surface can accordingly readily absorb radiation during the day and/or when the focused solar energy 127 is above a threshold level, and can transmit (e.g., by conduction) the absorbed energy to the second surface 663b. The second surface 663b can have a relatively low absorptivity and a relatively high emissivity can accordingly emit energy conducted to it by the first surface 663a. In one orientation, this effect can operate to heat the first reaction zone 611a, and in the opposite orientation, this effect can operate to cool the first reaction zone 611a (or another component of the reactor 110, e.g. the first heat exchanger 150a described above), for example, at night. Accordingly, the radiation control structure 660 can enhance the manner in which radiation is delivered to the first reaction zone 611a, and the manner in which heat is removed from the reactor 610.

In still further embodiments, the reactor 610 can include a redirection component 670 coupled to a redirection actuator 671 to redirect radiation that "spills" (e.g. is not precisely focused on the transmissive component 612) due to collector surface aberrations, environmental defects, non-parallel radiation, wind and/or other disturbances or distortions. In a particular embodiment, the redirection 670 can include movable elements 672 that pivot about corresponding pivot joints 674 in a Venetian blind arrangement generally similar to that discussed above. Accordingly, these elements 672 can be positioned circumferentially around the radiation-receiving surfaces of the reactor 610. In one aspect of this embodiment, the surfaces of the movable elements 672 are reflective in order to simply redirect radiation into the first reaction zone 611a. In other embodiments, the surfaces can include wavelength-shifting characteristics described above and described in co-pending U.S. patent application Ser. No. 13/027,015 titled "CHEMICAL REACTORS WITH RE-RADIATING SURFACES AND ASSOCIATED SYSTEMS AND METHODS" previously incorporated by reference.

One feature of embodiments of the systems and processes described above with reference to FIGS. 1-6 that they can use a solar collector or concentrator surface to provide cooling as well heating, in effect, operating the concentrator surface in reverse. This arrangement can provide a useful heat transfer process for cooling products and/or other constituents produced by the reactor, while reducing or eliminating the need for separate elements (e.g., refrigeration systems) to provide these functions.

Another feature of at least some of the foregoing embodiments is that they can include surfaces specifically tailored to enhance the absorption and/or emission of radiation entering or rejected by the system. These elements can provide further thermodynamic efficiencies and therefore reduce the cost of producing the reactants described above.

Certain aspects of the technology described in the context of particular embodiments may be combined or eliminated in other embodiments. For example, particular embodiments were described above in the context of a reactor having two reaction zones. In other embodiments, similar arrangements for rejecting heat can be applied to reactors having a single reaction zone, or more than two reaction zones. The reaction zone(s) can be used to process constituents other than those described above in other embodiments. The solar concentrators described above can be used for other cooling processes in other embodiments. The solar concentrators can have other configurations (e.g., heliostat configurations) in other embodiments. In at least some embodiments, the reaction zone(s) can move relative to the solar concentrator, in addition to or in lieu of the solar concentrator moving relative to the reaction zone(s). The redirection component and radiation control structures described above can be used alone, in combination with each other, and/or in combination with any of the arrangements described above in association with FIGS. 1-5.

Further, while advantages associated with certain embodiments of the technology have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

To the extent not previously incorporated herein by reference, the present application incorporates by reference in their entirety the subject matter of each of the following materials: U.S. patent application Ser. No. 12/857,553, filed on Aug. 16, 2010 and titled SUSTAINABLE ECONOMIC DEVELOPMENT THROUGH INTEGRATED PRODUCTION OF RENEWABLE ENERGY, MATERIALS RESOURCES, AND NUTRIENT REGIMES; U.S. patent application Ser. No. 12/857,553, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. patent application Ser. No. 12/857,554, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE MATERIAL RESOURCES USING SOLAR THERMAL; U.S. patent application Ser. No. 12/857,502, filed on Aug. 16, 2010 and titled ENERGY SYSTEM FOR DWELLING SUPPORT; Ser. No. 13/027,235, filed on Feb. 14, 2011 and titled DELIVERY SYSTEMS WITH IN-LINE SELECTIVE EXTRACTION DEVICES AND ASSOCIATED METHODS OF OPERATION; U.S. Patent Application No. 61/401,699, filed on Aug. 16, 2010 and titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES; Ser. No. 13/027,028, filed on Feb. 14, 2011 and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS; Ser. No. 13/026,996, filed on Feb. 14, 2011 and titled REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS; Ser. No. 13/027,015, filed on Feb. 14, 2011 and titled CHEMICAL REACTORS WITH RE-RADIATING SURFACES AND ASSOCIATED SYSTEMS AND METHODS; Ser. No. 13/027,244, filed on Feb. 14, 2011 and titled THERMAL TRANSFER DEVICE AND ASSOCIATED SYSTEMS AND METHODS; Ser. No. 13/026,990, filed on Feb. 14, 2011 and titled CHEMICAL REACTORS WITH ANNULARLY POSITIONED DELIVERY AND REMOVAL DEVICES, AND ASSOCIATED SYSTEMS AND METHODS; Ser. No. 13/027,215, filed on Feb. 14, 2011 and titled INDUCTION FOR THERMOCHEMICAL PROCESS, AND ASSOCIATED SYSTEMS AND METHODS; Ser. No. 13/027,198, filed on Feb. 14, 2011 and titled COUPLED THERMOCHEMICAL REACTORS AND ENGINES, AND ASSOCIATED SYSTEMS AND METHODS; U.S. Patent Application No. 61/385,508, filed on Sep. 22, 2010 and titled REDUCING AND HARVESTING DRAG ENERGY ON MOBILE ENGINES USING THERMAL CHEMICAL REGENERATION; Ser. No. 13/027,060, filed on Feb. 14, 2011 and titled REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS; Ser. No. 13/027,214, filed on Feb. 14, 2011 and titled ARCHITECTURAL CONSTRUCT HAVING FOR EXAMPLE A PLURALITY OF ARCHITECTURAL CRYSTALS; U.S. patent application Ser. No. 12/806,634, filed on Aug. 16, 2010 and titled METHODS AND APPARATUSES FOR DETECTION OF PROPERTIES OF FLUID CONVEYANCE SYSTEMS; Ser. No. 13/027,188, filed on Feb. 14, 2011 and titled METHODS, DEVICES, AND SYSTEMS FOR DETECTING PROPERTIES OF TARGET SAMPLES; Ser. No. 13/027,068, filed on Feb. 14, 2011 and titled SYSTEM FOR PROCESSING BIOMASS INTO HYDROCARBONS, ALCOHOL VAPORS, HYDROGEN, CARBON, ETC.; Ser. No. 13/027,196, filed on Feb. 14, 2011 and titled CARBON RECYCLING AND REINVESTMENT USING THERMOCHEMICAL REGENERATION; Ser. No. 13/027,195, filed on Feb. 14, 2011 and titled OXYGENATED FUEL; U.S. Patent Application No. 61/237,419, filed on Aug. 27, 2009 and titled CARBON SEQUESTRATION; U.S. Patent Application No. 61/237,425, filed on Aug. 27, 2009 and titled OXYGENATED FUEL PRODUCTION; Ser. No. 13/027,197, filed on Feb. 14, 2011 and titled MULTI-PURPOSE RENEWABLE FUEL FOR ISOLATING CONTAMINANTS AND STORING ENERGY; U.S. Patent Application No. 61/421,189, filed on Dec. 8, 2010 and titled LIQUID FUELS FROM HYDROGEN, OXIDES OF CARBON, AND/OR NITROGEN; AND PRODUCTION OF CARBON FOR MANUFACTURING DURABLE GOODS; and Ser. No. 13/027,185, filed on Feb. 14, 2011 and titled ENGINEERED FUEL STORAGE, RESPECIATION AND TRANSPORT.

I claim:

1. A reactor system for processing a reactant, comprising:
a reactor having a reaction zone;
a reactant source coupled in fluid communication with the reaction zone of the reactor;
a solar concentrator having at least one concentrator surface positionable to direct solar energy to a focal area;
an actuator coupled to the solar concentrator to move the solar concentrator relative to the sun; and
a controller operatively coupled to the actuator, the controller being programmed with instructions that, when executed:
direct the actuator to position the solar concentrator to focus the solar energy on the reaction zone when the solar energy is above a threshold level; and
direct the actuator to position the solar concentrator to point to a location in the sky having relatively little radiant energy to cool an object positioned at the focal area when the solar energy is below the threshold level.

2. The system of claim 1, further comprising a heat exchanger carrying a heat exchanger fluid, and wherein the heat exchanger is positionable at the focal area when the solar energy is below the threshold level to discharge heat from the heat exchanger fluid via the solar concentrator.

3. The system of claim 2 wherein at least one of the heat exchanger and the solar concentrator is movable relative to the other between a first configuration in which the focal area is aligned with the reaction zone and a second configuration in which the focal area is aligned with the heat exchanger.

4. The system of claim 1 wherein the reaction zone is a first reaction zone and wherein the system further includes a second reaction zone, and wherein at least one of the solar concentrator, the first reaction zone and the second reaction zone is movable to form a first configuration in which the focal area is aligned with the first reaction zone and a second configuration in which the focal area is aligned with the second reaction zone.

5. The system of claim 1, further comprising a reactant carried by the reactant source, and wherein the reactant includes a hydrogen donor having at least one of carbon, boron, nitrogen, silicon, a transition metal, and sulfur as a constituent.

6. The system of claim 1 wherein the solar concentrator includes a dish-shaped concentrator.

7. The system of claim 1 wherein the solar concentrator includes a trough-shaped concentrator.

8. The system of claim 1 wherein the solar concentrator includes a Fresnel lens.

9. A reactor system for processing a reactant, comprising:
a reactor having a reaction zone;
a reactant source coupled in fluid communication with the reaction zone of the reactor;
a solar concentrator having at least one concentrator surface positionable to direct solar energy to a focal area;
a first actuator coupled to the solar concentrator to move the solar concentrator relative to the sun;
a radiation control structure positioned between the concentrator surface and the focal area, the radiation control structure having a first surface and a second surface facing away from the first surface, the first surface having a first radiant energy absorptivity and a first radiant energy emissivity, the second surface having a second radiant energy absorptivity less than the first radiant energy absorptivity and a second radiant energy emissivity greater than the first radiant energy emissivity; and
a second actuator coupled to the radiation control structure to change the structure from a first configuration in which the first surface faces toward the concentrator surface, and a second configuration in which the second surface faces toward the concentrator surface.

10. The system of claim 9, further comprising:
a controller operatively coupled to the first and second actuators, the controller being programmed with instructions that, when executed:
direct the first actuator to position the solar concentrator to focus the solar energy on the reaction zone when the solar energy is above a threshold level;
direct the second actuator to position the radiation control structure in the first configuration when the solar energy is above the threshold level;
direct the first actuator to position the solar concentrator to point to a location in the sky away from the sun and having relatively little radiant energy to cool an object positioned at the focal area when the solar energy is below the threshold level; and
direct the second actuator to position the radiation control structure in the second configuration when the solar energy is below the threshold level.

11. The system of claim 10 wherein the radiation control structure includes a plurality of pivotable elements, and wherein individual pivotable elements have a first surface and a second surface facing away from the first surface.

12. The system of claim 9, further comprising a redirection component positioned proximate to the solar concentrator and the reaction zone, the redirection component having at least one movable surface positioned to receive at least a portion of the solar energy directed by the solar concentrator and redirect the portion of energy into the reaction zone.

13. The system of claim 12 wherein the redirection component includes a plurality of movable surfaces.

14. The system of claim 13 wherein the movable surfaces include reflective surfaces.

15. The system of claim 13 wherein the movable surfaces include a re-radiation component positioned to receive radiation over a first spectrum having a first peak wavelength range and re-radiate the radiation into the reaction zone over a second spectrum having a second peak wavelength range different than the first.

16. The system of claim 9, further comprising a reactant carried by the reactant source, and wherein the reactant includes a hydrogen donor having at least one of carbon, boron, nitrogen, silicon, a transition metal, and sulfur as a constituent.

17. A reactor system for processing a hydrogen donor, comprising:
a reactor vessel having a reaction zone;
a hydrocarbon donor source coupled in fluid communication with the reaction zone of the reactor vessel and carrying a hydrocarbon donor;
a first product collector coupled to the reaction zone to receive a hydrogen-based fuel produced by dissociating the hydrogen donor at the reaction zone;
a second product collector coupled to the reaction zone to receive at least one of carbon and a carbon compound produced by dissociating the hydrogen donor;
a solar concentrator having at least one concentrator surface having a focal area and being positionable to direct solar energy toward the reaction zone;
an actuator coupled to the solar concentrator to move the solar concentrator relative to the sun; and
a controller operatively coupled to the actuator, the controller being programmed with instructions that, when executed:
direct the solar concentrator to point toward the sun and focus the solar energy on the reaction zone during daylight hours; and
direct the solar concentrator to point to a location in the sky having relatively little radiation energy to cool an object positioned at the focal area after daylight hours.

18. The system of claim 17, wherein the reaction zone includes a first reaction zone, the actuator includes a first actuator and wherein the system further includes a second reaction zone, and wherein the system further comprises:
a heat exchanger carrying a heat exchanger fluid in fluid communication with the second reaction zone; and
a second actuator coupled to at least one of the heat exchanger and the solar concentrator; and wherein the controller is programmed with further instructions that, when executed:
direct the second actuator to align the focal area with the first reaction zone during daylight hours; and
direct the second actuator to align the focal area with the heat exchanger after daylight hours.

* * * * *